US011986166B2

(12) United States Patent
Abdolahad et al.

(10) Patent No.: US 11,986,166 B2
(45) Date of Patent: May 21, 2024

(54) REAL-TIME DIAGNOSIS OF CANCER INVOLVED SENTINEL LYMPH NODES (SLNS) BASED ON pH SENSING

(71) Applicants: Mohammad Abdolahad, Tehran (IR); Zohreh Sadat Miripour, Tehran (IR); Parisa Aghaee, Tehran (IR)

(72) Inventors: Mohammad Abdolahad, Tehran (IR); Zohreh Sadat Miripour, Tehran (IR); Parisa Aghaee, Tehran (IR)

(73) Assignee: NANO HESGARSAZAN SALAMAT ARYA (IR)

( * ) Notice: Subject to any disclaimer, the term of this patent is extended or adjusted under 35 U.S.C. 154(b) by 79 days.

(21) Appl. No.: 17/195,680

(22) Filed: Mar. 9, 2021

(65) Prior Publication Data

US 2021/0223246 A1    Jul. 22, 2021

Related U.S. Application Data

(60) Provisional application No. 62/987,884, filed on Mar. 11, 2020.

(51) Int. Cl.
*A61B 5/1473*    (2006.01)
*A61B 5/00*    (2006.01)
(Continued)

(52) U.S. Cl.
CPC ...... *A61B 10/0041* (2013.01); *A61B 5/14539* (2013.01); *A61B 5/1473* (2013.01); *A61B 5/418* (2013.01); *A61M 2202/0405* (2013.01)

(58) Field of Classification Search
CPC ... A61B 5/14539; A61B 5/1473; A61B 5/418; A61B 5/1482; A61B 5/1411; A61B 5/1422; A61B 5/14503; A61B 5/145; A61B 5/14507; A61B 5/1451; A61B 5/14532; A61B 5/14546; A61B 5/1468; A61B 5/1486; A61B 10/0041; A61B 10/45; A61B 2562/0295; A61M 2202/0405; A61F 2013/423; A61F 2013/427

See application file for complete search history.

(56) References Cited

U.S. PATENT DOCUMENTS

| 7,344,499 B1 * | 3/2008 | Prausnitz ......... A61B 5/150022 600/347 |
| 2008/0154102 A1 * | 6/2008 | Frangioni ............ A61B 5/0073 600/317 |

(Continued)

FOREIGN PATENT DOCUMENTS

| KR | 20190133338 A | * 12/2019 | |
| WO | WO-2013167587 A1 | * 11/2013 | ............. G01N 24/08 |

*Primary Examiner* — Puya Agahi
*Assistant Examiner* — Grace L Rozanski

(57) ABSTRACT

A method for detecting cancer involved lymph nodes. The method includes placing a pH-sensing paper inside a needle of an injection syringe, filling the injection syringe with a buffer solution, putting the pH-sensing paper in contact with lymphatic fluid of a lymph node by inserting the needle of the injection syringe inside the lymph node, putting the lymphatic fluid in interaction with the buffer solution by injecting the buffer solution into the lymph node utilizing the injection syringe, and detecting that the lymph node as a cancer involved lymph node if color of the pH-sensing paper is changed to an acidic-range pH color.

9 Claims, 8 Drawing Sheets

REAL-TIME DIAGNOSIS OF CANCER INVOLVED SENTINEL LYMPH NODES (SLNS) BASED ON PH SENSING

100

(51) Int. Cl.
*A61B 5/145* (2006.01)
*A61B 10/00* (2006.01)

(56) References Cited

U.S. PATENT DOCUMENTS

| | | | |
|---|---|---|---|
| 2009/0209489 A1* | 8/2009 | Brown | A61K 31/7008 514/23 |
| 2015/0031014 A1* | 1/2015 | Lu | G01N 33/581 435/5 |
| 2016/0080548 A1* | 3/2016 | Erickson | H04M 1/72409 382/128 |
| 2019/0076631 A1* | 3/2019 | McHugh | A61M 31/002 |
| 2019/0175104 A1* | 6/2019 | Malik | A61B 5/145 |

* cited by examiner

REAL-TIME DIAGNOSIS OF CANCER INVOLVED SENTINEL LYMPH NODES (SLNS) BASED ON PH SENSING

REAL-TIME DIAGNOSIS OF CANCER INVOLVED SENTINEL LYMPH NODES (SLNS) BASED ON pH SENSING

CROSS-REFERENCE TO RELATED APPLICATION

This application claims the benefit of priority from U.S. Provisional Patent Application Ser. No. 62/987,884 filed on Mar. 11, 2020, and entitled "REAL-TIME DIAGNOSIS OF SENTINEL LYMPH NODES INVOLVED WITH BREAST CANCER BASED ON PH SENSING THROUGH LIPID SYNTHESIS OF THOSE CELLS", which is incorporated herein by reference in its entirety.

TECHNICAL FIELD

The present disclosure generally relates to cancer diagnosis, and particularly, to detecting a cancer involved sentinel lymph node (SLN) by sensing and/or measuring pH value of lymph node fluid.

BACKGROUND

Lymph nodes are small glands that filter lymphatic fluid which is a clear fluid that circulates through the lymphatic system. The lymphatic system, part of the immune system, is a network of ducts that carry the lymphatic fluid (LF). LF also contains white blood cells called lymphocytes, fats, and proteins. The lymphatic system extracts LF from the body and after purifying it from infectious organisms and abnormal cells, carries it into the bloodstream. In many types of cancers, especially breast carcinoma, a lymph node is the first location being invaded by cancer cells through lymphatic vessels. Hence, breast tumor invasion to a sentinel lymph node (SLN) is the first sign of disease progression and metastasis. So, detection of lymph node metastasis is crucial in designation of treatment protocol by an oncologist.

Although SLN involvement may be found during an interventional radiology (Ultrasonography and biopsy) in many cases, it is mandatory to dissect the SLNs (either it is involved or free in biopsy result) in patients with invasive breast carcinoma to be sent for intraoperative frozen section. If the SLN is involved, the surgeon must dissect at least six auxiliary lymph nodes (ALNs) and if the SLNs are free from cancer cells it is not mandatory to dissect further lymph nodes.

Currently, the only common method for detection of metastatic cancer cells in lymph (sentinel and auxiliary) nodes during surgery is frozen pathology which is highly dependent on the experience and skills of a pathologist. Due to the lack of time in a frozen section to respond to a surgeon, just a part of a removed lymph node (due to color, stiffness, and firmness) is often selected for frozen examination. So, in some cases, pathological mistakes in missing an involved LNs might be occurred in the frozen section, and cancer cells might be missed and assumed as histiocytes.

So, there is a lack of a real-time noninvasive, simple and reliable method to detect metastatic lymph nodes. Hence, there is a need for an instrument, method and system that is capable of detecting cancer involved LNs via an accurate, real-time responding, noninvasive, uncomplicated, and reliable approach. Furthermore, there is a need for an instrument, method and system for accurate diagnosis of cancer involved lymph nodes to prevent from removing normal lymph nodes and/or remaining cancer involved lymph nodes, which are crucial in programming a treating procedure of a patient.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for detecting cancer involved lymph nodes. The method may include measuring pH value of lymphatic fluid of a lymph node and detecting that the lymph node may be a cancer involved lymph node if the measured pH value of the lymphatic fluid is less than 7.0.

In another general aspect, an exemplary method for detecting cancer involved lymph nodes is disclosed. In an exemplary implementation, the method may include measuring pH value of lymphatic fluid of a lymph node and detecting that the lymph node may be a cancer involved lymph node if the measured pH value of the lymphatic fluid is less than 7.0. In an exemplary implementation, measuring pH value of the lymphatic fluid of the lymph node may include putting the lymphatic fluid of the lymph node in interaction with a buffer solution by injecting the buffer solution into the lymph node and measuring pH value of the interacted lymphatic fluid with the buffer solution by inserting a pH-sensing paper inside the lymph node. In an exemplary implementation, detecting that the lymph node may be a cancer involved lymph node if the measured pH value of the lymphatic fluid is less than 7.0 may include detecting that the lymph node may be a cancer involved lymph node if a color of the pH-sensing paper is changed to an acidic-range pH color.

In an exemplary implementation, putting the lymphatic fluid of the lymph node in interaction with the buffer solution may include injecting a biocompatible buffer solution with a neutral pH value to the lymph node utilizing a syringe. In an exemplary implementation, putting the lymphatic fluid of the lymph node in interaction with the buffer solution may include injecting at least 100 µl of a sterile buffer solution of phosphate-buffered saline (PBS) into the lymph node. In an exemplary implementation, injecting the buffer solution into the lymph node may include injecting the buffer solution into a lymph node located at least one of armpits, digestive system, groin, neck, and combinations thereof. In an exemplary implementation, injecting the buffer solution into the lymph node may include at least one of in vitro injecting the buffer solution into the lymph node and in vivo injecting the buffer solution into the lymph node, and combinations thereof.

In an exemplary implementation, measuring pH value of the interacted lymphatic fluid with the buffer solution by inserting a pH-sensing paper inside the lymph node may include placing the pH-sensing paper inside a hypodermic needle, inserting the hypodermic needle into the lymph node, and detecting changes in color of the pH-sensing paper for a time period between 5 seconds and 30 seconds.

In another general aspect, another exemplary implementation of an exemplary method for detecting cancer involved lymph nodes is disclosed. In an exemplary implementation, the method may include placing a pH-sensing paper inside a needle of an injection syringe, filling the injection syringe with a buffer solution, putting the pH-sensing paper in contact with lymphatic fluid of a lymph node by inserting the needle of the injection syringe inside the lymph node, putting the lymphatic fluid in interaction with the buffer solution by injecting the buffer solution into the lymph node utilizing the injection syringe, and detecting that the lymph node may be a cancer involved lymph node if color of the pH-sensing paper is changed to an acidic-range pH color.

In an exemplary implementation, injecting the buffer solution into the lymph node may include injecting a sterile buffer solution of phosphate-buffered saline (PBS) into the lymph node. In an exemplary implementation, injecting the sterile buffer solution into the lymph node may include injecting at least 100 µL of the PBS into the lymph node. In an exemplary implementation, injecting the buffer solution into the lymph node may include injecting the buffer solution into a lymph node located at least one of armpits, digestive system, groin, neck, and combinations thereof.

In an exemplary implementation, injecting the buffer solution into the lymph node may include at least one of in vitro injecting the buffer solution into the lymph node and in vivo injecting the buffer solution into the lymph node, and combinations thereof.

In an exemplary implementation, the method may further include detecting (recording) changes in color of the pH-sensing paper for a time period between 5 seconds and 30 seconds after injecting the buffer solution into the lymph node.

In an exemplary implementation, the needle of the injection syringe may include a hypodermic needle with a gauge size 18.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
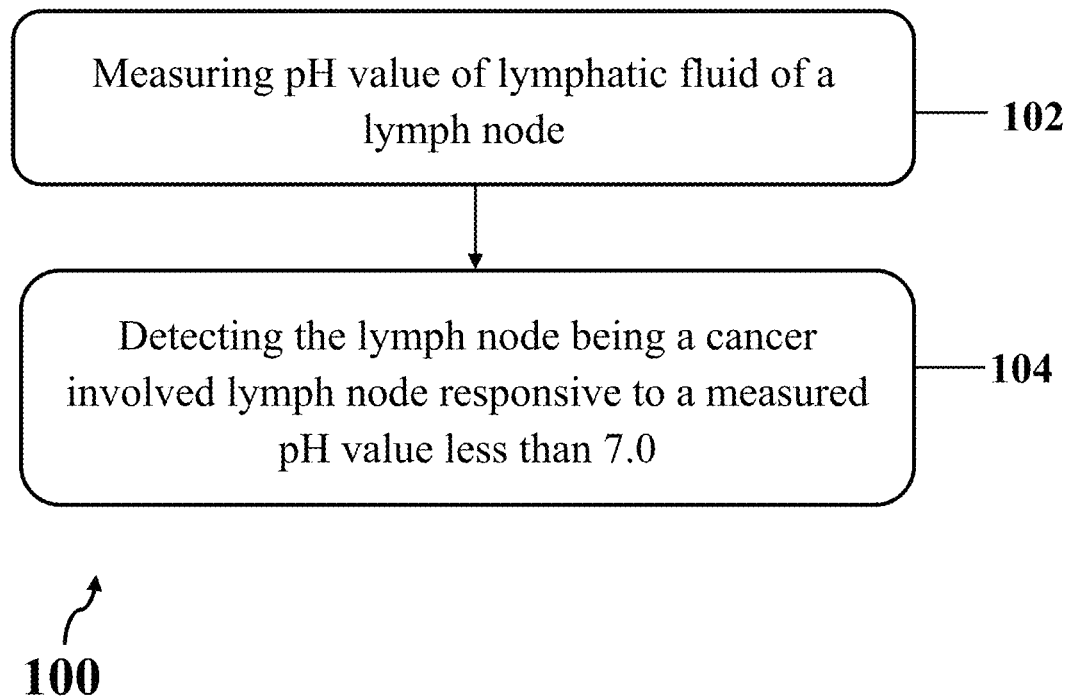
FIG. 1 illustrates an exemplary method for detecting cancer involved lymph nodes (LNs) in a person's body that may be suspected to have cancer, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Early detection of cancer involved lymph nodes (LNs) is crucial in preparing a therapeutical and treatment plan for a cancer patient. Metabolism of cancer cells metastasize to LNs is very complicated. Metabolism of cancer cells metastasized to LNs is changed from glycolysis to fatty acid oxidation (FAO). Expression of Yes-Associated Protein (YAP) selectively activates FAO-related genes in metastatic lymphatic tumors. Consequently, activated FAO-related genes in tumors that have metastasized to lymph will stimulate metabolism toward FAO rather than glycolysis. As a result of activation of FAO, environment of a metastasized lymph node would be acidic.

Herein, an exemplary real-time, reliable and simple diagnostic instrument and method is disclosed for cancer diagnosis by detecting cancer involved lymph nodes via pH sensing in lymph. Herein, "cancer involved LNs" may refer to either a cancerous lymph node, or a lymph node invaded by metastatic cancer cells, or in other words, metastasis of cancer cells to a lymph node. An exemplary instrument and an exemplary method based on acidification of cancer involved LNs due to fatty acid oxidation metabolism of cancer cells in LNs are disclosed here. An exemplary method may include calibrating live pH of SLNs by pathological assays results, so exemplary method may allow for diagnosing metastatic SLNs with no need for any lymph node dissection prior to cancer diagnosis. An exemplary method described herein may allow for preserving free SLNs for the patient, whereas through frozen method even if a SLN is free from a tumor or cancer cells, a patient looses his/her SLNs which may cause many side effects for him/her such as lymphedema, lost or decreased sensation in back of arm or armpit region, and tingling, numbness, stiffness in armpit, etc. In an exemplary implementation, an exemplary method may be disclosed for diagnosis of breast cancer via measuring pH value of lymphatic fluid of a lymph node at armpits. Exemplary method may be based on metastasis and invasion of breast cancer cells to SLNs at armpits, so that an acidic pH may be detected for SLNs due to metabolism of cancer cells there.

FIG. 1 shows exemplary method 100 for detecting cancer involved lymph nodes in a person's body that may be suspected to have cancer, consistent with one or more exemplary embodiments of the present disclosure. Exemplary method 100 may include measuring pH value of lymphatic fluid of a lymph node (step 102) and detecting the lymph node is a cancer involved lymph node if the measured pH value is less than about 7.0 (step 104).

In detail, step 102 may include measuring pH value of lymphatic fluid inside a lymph node. The lymph node may be located throughout of a person's body, where the largest groups of lymph nodes may be located in neck, groin, and armpits areas. In an exemplary implementation, measuring pH value of lymphatic fluid inside the lymph node may include measuring pH value of lymphatic fluid of lymphatic system of the person's body. In an exemplary implementation, measuring pH value of lymphatic fluid inside the lymph node may include measuring pH value of lymphatic fluid of one or more lymph nodes of the lymphatic system throughout the person's body.

In an exemplary implementation, method 100 may be done through an in vitro procedure or an in vivo procedure. In an exemplary implementation, step 102 may include in vitro measuring pH value of lymphatic fluid inside a resected lymph node from a person's body or a dissected lymph node of a person's body. In another exemplary implementation, step 102 may include in vivo measuring pH value of lymphatic fluid inside a lymph node of a person's body without any need to utilize an invasive procedure. Further details of step 102 are provided further below in context of FIGS. 2-5.

In an exemplary implementation, in vitro measuring pH value of lymphatic fluid inside the resected lymph node from the person's body or the dissected lymph node of the person's body may include resecting a lymph node of the person's body, and measuring pH value of lymphatic fluid of the resected lymph node. In an exemplary implementation, measuring pH value of the lymphatic fluid of the resected lymph node may include putting the lymphatic fluid of the resected lymph node in interaction with a buffer solution by injecting the buffer solution to the resected lymph node, putting the interacted lymphatic fluid of the lymph node with the buffer solution in contact with a pH-sensing paper, and measuring pH value of the lymphatic fluid by recording color of the pH-sensing paper.

In an exemplary implementation, in vivo measuring pH value of lymphatic fluid of the lymph node may include putting the lymphatic fluid of the lymph node in interaction with a buffer solution by injecting the buffer solution to the lymph node, putting the interacted lymphatic fluid of the lymph node with the buffer solution in contact with a pH-sensing paper, and measuring pH value of the lymphatic fluid by recording color of the pH-sensing paper.

In an exemplary implementation, measuring pH value of the lymphatic fluid may include determining an acidic pH value for the lymphatic fluid if the recorded color of the pH-sensing paper is changed to a color spectrum from yellow to red. In an exemplary implementation, measuring pH value of the lymphatic fluid may include determining a basic or alkali pH value for the lymphatic fluid if the recorded color of the pH-sensing paper is changed to a color spectrum from blue to violet. In an exemplary implementation, measuring pH value of the lymphatic fluid may include determining a neutral pH value for the lymphatic fluid if the recorded color of the pH-sensing paper is remained unchanged with a green color.

Furthermore, step 104 may include detecting the lymph node as a cancer involved lymph node if the measured pH value is less than about 7.0. In an exemplary implementation, detecting the lymph node as a cancer involved lymph node may include comparing the measured pH value of the lymphatic fluid with a neutral pH value of 7.0 and detecting the lymph node as a cancer involved lymph node if the measured pH value of the lymphatic fluid is an acidic pH value of less than 7.0. In an exemplary implementation, the lymph node may be detected as a cancer involved lymph node if the measured pH value of the lymphatic fluid is equal to 6.0 or less. In an exemplary implementation, detecting the lymph node as a cancer involved lymph node may include detecting an acidic-range color spectrum of a pH-sensing paper in contact with the lymphatic fluid of the lymph node in a spectrum from yellow to red.

In an exemplary implementation, detecting the lymph node as a cancer involved lymph node (step 104) may include detecting the lymph node to be either a cancerous lymph node or a lymph node that may be involved to cancer by a cancer metastasis to lymphatic system of a patient if the measured pH value of lymphatic fluid inside the lymph node is an acidic pH value. In an exemplary embodiment, when metastatic cancer cells invade to lymphatic system, cancer cells may enter inside a lymph node and the lymph node may become a metastatic lymph node or a cancer involved lymph node. Consequently, expression of YAP may selectively activate FAO-related genes in lymphatic metastatic cancer cells and the lymphatic metastatic cancer cells may use plentiful fatty acids as fuel. This phenomenon may result in acidity of lymphatic fluid of the metastatic lymph node (the cancer involved lymph node).

Figure 2:
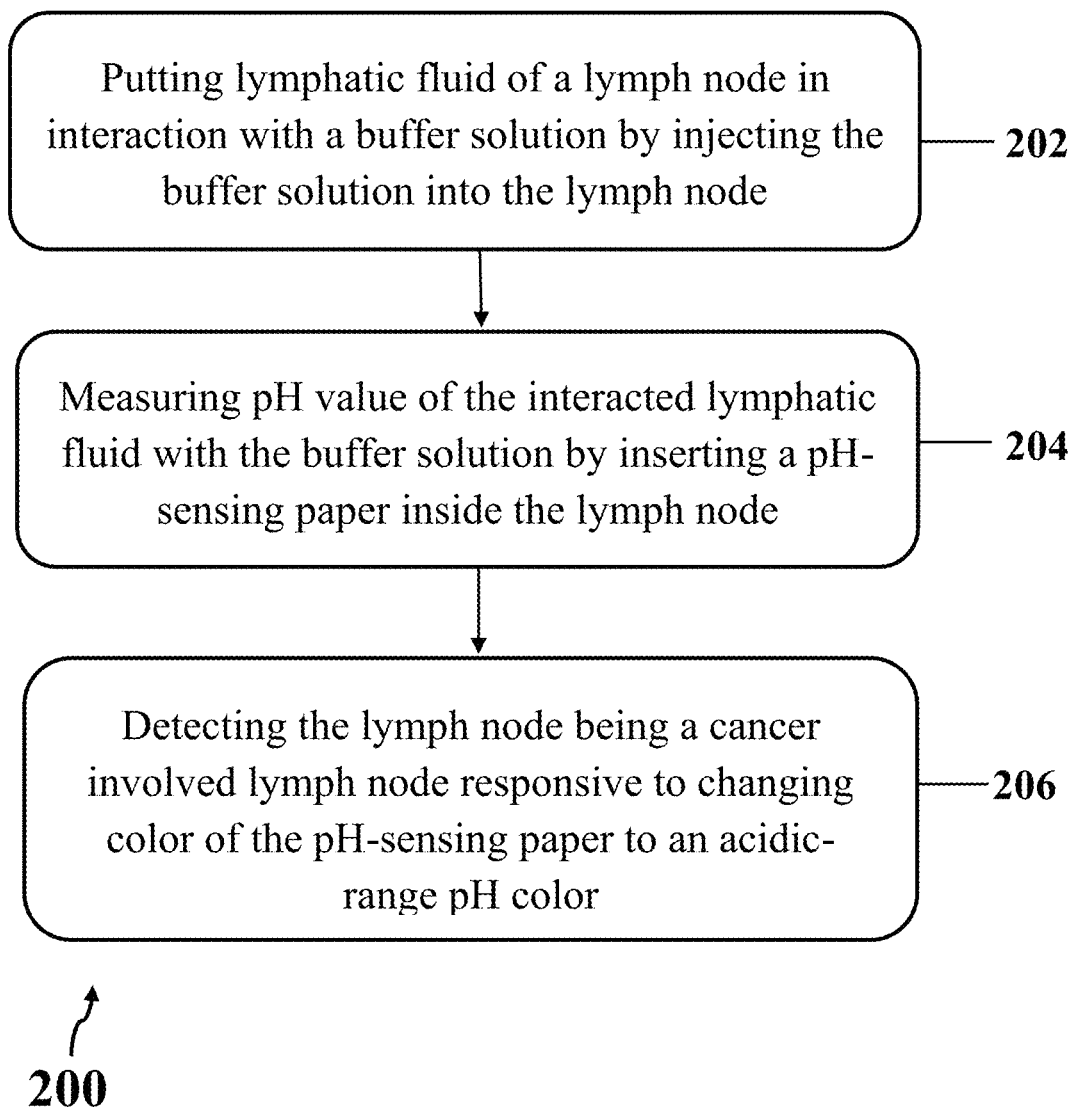
FIG. 2 illustrates an exemplary implementation of an exemplary method for detecting cancer involved lymph nodes, consistent with one or more exemplary embodiments of the present disclosure.

FIG. 2 shows an exemplary implementation 200 of method 100 for detecting cancer involved lymph nodes, consistent with one or more exemplary embodiments of the present disclosure. Exemplary method 200 may include putting lymphatic fluid of a lymph node in interaction with a buffer solution by injecting the buffer solution into the lymph node (step 202), measuring pH value of the interacted lymphatic fluid with the buffer solution by inserting a pH-sensing paper inside the lymph node (step 204), and detecting the lymph node as a cancer involved lymph node if color of the pH-sensing paper is changed to an acidic-range pH color (step 206).

Regarding FIGS. 1 and 2, in an exemplary implementation, step 102 of method 100 may include putting lymphatic fluid of the lymph node in interaction with the buffer solution by injecting the buffer solution into the lymph node (step 202) and measuring pH value of the interacted lymphatic fluid with the buffer solution by inserting the pH-sensing paper inside the lymph node (step 204). Moreover, in an exemplary implementation, step 104 of method 100 may include step 206 including detecting the lymph node as a cancer involved lymph node if color of the pH-sensing paper is changed to an acidic-range pH color.

In detail, step 202 may include putting lymphatic fluid of a lymph node in interaction with a buffer solution by injecting the buffer solution into the lymph node. In an exemplary implementation, putting lymphatic fluid of the lymph node in interaction with the buffer solution may include putting lymphatic fluid of the lymph node in interaction with a biocompatible and sterile buffer solution with a neutral pH value. In an exemplary implementation, putting lymphatic fluid of the lymph node in interaction with the buffer solution may include putting lymphatic fluid of the lymph node in interaction with phosphate-buffered saline (PBS) solution. In an exemplary implementation, putting lymphatic fluid of the lymph node in interaction with the buffer solution may include injecting PBS solution into the lymph node. In an exemplary implementation, putting lymphatic fluid of the lymph node in interaction with the buffer solution may include injecting an amount of the buffer solution between about 20 μL and 200 μL into the lymph node.

In an exemplary implementation, putting lymphatic fluid of the lymph node in interaction with the buffer solution may include injecting the buffer solution to the lymph node immediately after resection or dissection of the lymph node through an in vitro procedure. In an exemplary implementation, putting lymphatic fluid of the lymph node in interaction with the buffer solution may include injecting the buffer solution to a person's body at a location of the lymph node through an in vivo procedure.

Moreover, step 204 may include measuring pH value of the interacted lymphatic fluid with the buffer solution by inserting a pH-sensing paper (a pH-indicator strip) inside the lymph node. In an exemplary implementation, inserting the pH-sensing paper inside the lymph node may include putting the interacted lymphatic fluid with the buffer solution in contact with the pH-sensing paper. In an exemplary implementation, inserting the pH-sensing paper inside the lymph node may include putting the interacted lymphatic fluid with the buffer solution in contact with the pH-sensing paper for a time period between about 5 seconds and 30 seconds. In an exemplary implementation, inserting the pH-sensing paper inside the lymph node may include putting the interacted lymphatic fluid with the buffer solution in contact with a Litmus paper.

Furthermore, step 206 may include detecting the lymph node as a cancer involved lymph node if color of the pH-sensing paper is changed to an acidic-range pH color. In an exemplary implementation, detecting the lymph node as the cancer involved lymph node may include detecting an acidic color for the pH-sensing paper in contact with the interacted lymphatic fluid with the buffer solution. In an exemplary implementation, detecting the lymph node as the cancer involved lymph node may include recording changes in color of the pH-sensing paper in contact with the interacted lymphatic fluid with the buffer solution over a period of time between about 5 seconds and about 30 seconds and detecting the lymph node as a cancer involved lymph node if the recorded changes in color of the pH-sensing paper in contact with the interacted lymphatic fluid with the buffer solution include a color change of the pH-sensing paper from a neutral pH indicating color to an acidic pH indicating color. In an exemplary implementation, detecting the lymph node as a cancer involved lymph node may include detecting a color change for the pH-sensing paper in contact with the interacted lymphatic fluid with the buffer solution from green to a color in a color spectrum from yellow to red.

Figure 3:
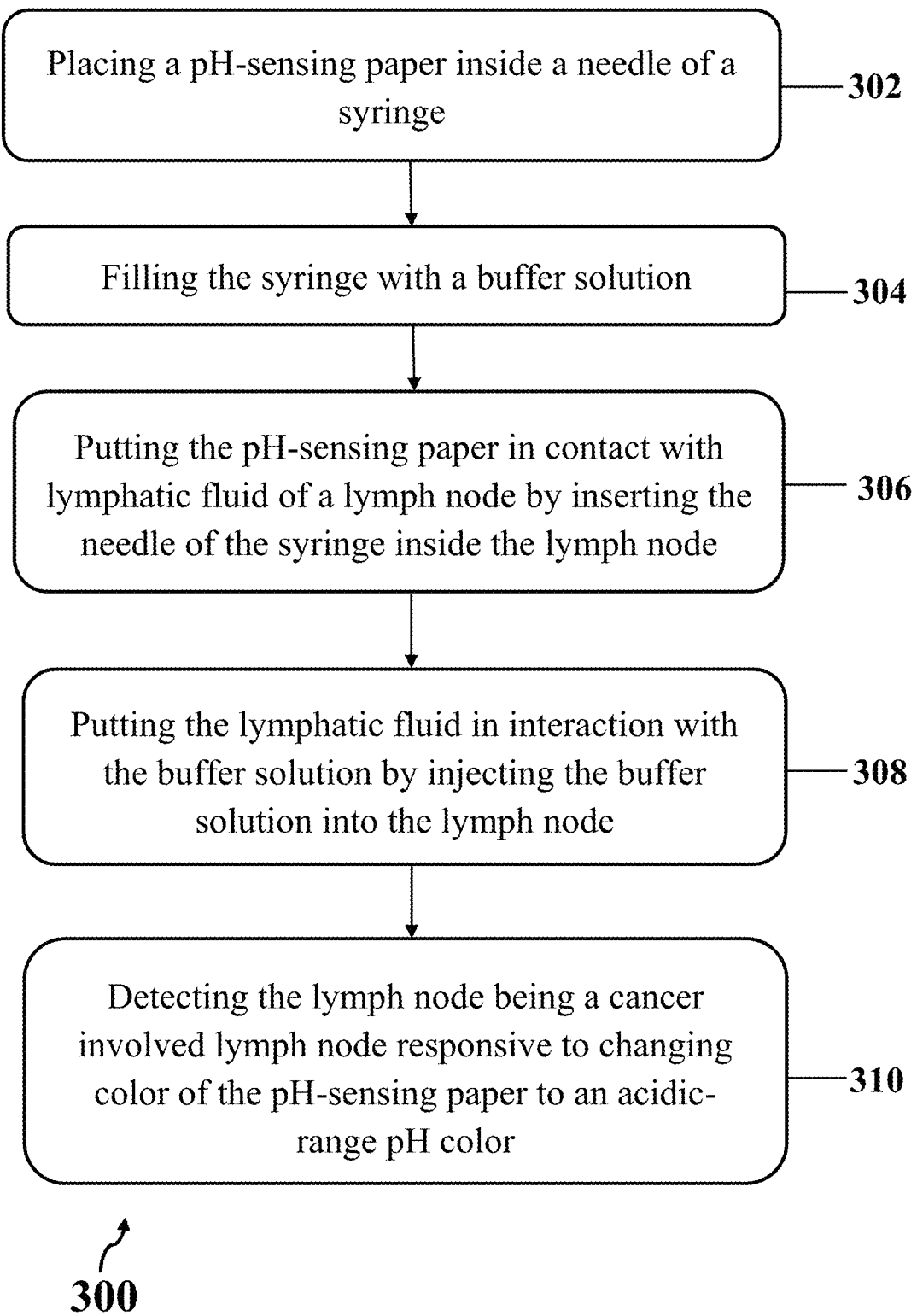
FIG. 3 illustrates an exemplary implementation of an exemplary method for detecting cancer involved lymph nodes, consistent with one or more exemplary embodiments of the present disclosure.

FIG. 3 shows an exemplary implementation 300 of method 200 for detecting cancer involved lymph nodes, consistent with one or more exemplary embodiments of the present disclosure. Exemplary method 300 may include placing a pH-sensing paper inside a needle of a syringe (step 302), filling the syringe with a buffer solution (step 304), putting the pH-sensing paper in contact with lymphatic fluid of a lymph node by inserting the needle of the syringe inside the lymph node (step 306), putting the lymphatic fluid in interaction with the buffer solution by injecting the buffer solution into the lymph node utilizing the syringe (step 308), and detecting the lymph node as a cancer involved lymph node if color of the pH-sensing paper is changed to an acidic-range pH color (step 310).

In an exemplary implementation, exemplary steps 302 to 310 of method 300 may correspond to exemplary steps 202 to 206 of method 200 but not in order. In an exemplary implementation regarding FIGS. 2 and 3, step 202 may include steps 304 and 308, including filling a syringe with a buffer solution (step 304) and putting lymphatic fluid of a lymph node in interaction with the buffer solution by injecting the buffer solution into the lymph node utilizing the syringe (step 308). In an exemplary implementation, step 204 may include steps 302 and 306, including placing a pH-sensing paper inside a needle of the syringe (step 302) and putting the pH-sensing paper in contact with lymphatic fluid of the lymph node by inserting the needle of the syringe inside the lymph node (step 306). In an exemplary implementation, step 206 may include step 310, including detecting the lymph node as a cancer involved lymph node if color of the pH-sensing paper is changed to an acidic-range pH color.

In detail, step 302 may include placing a pH-sensing paper inside a needle of a syringe. In an exemplary implementation, placing the pH-sensing paper inside the needle of the syringe may include embedding the pH-sensing paper inside a hollow needle of a hypodermic needle that may be configured to be attached to a syringe. In an exemplary embodiment, the hypodermic needle including the pH-sensing paper embedded there inside may be a simple non-invasive tool for precise and fast diagnosis of cancer involved LNs.

Figure 4A:
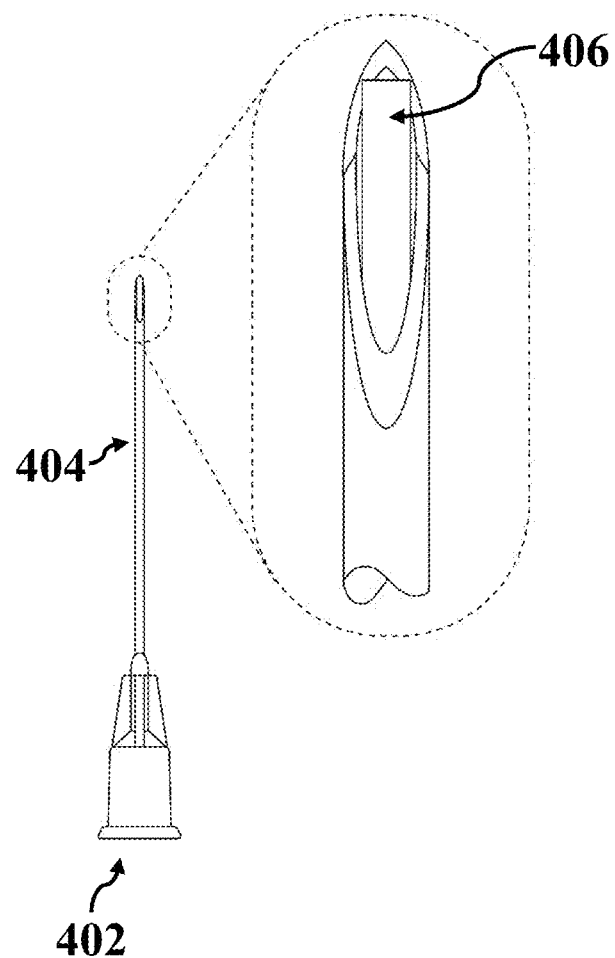
FIG. 4A illustrates a schematic view of an exemplary instrument for diagnosis of cancer involved LNs, consistent with one or more exemplary embodiments of the present disclosure.
Figure 4B:
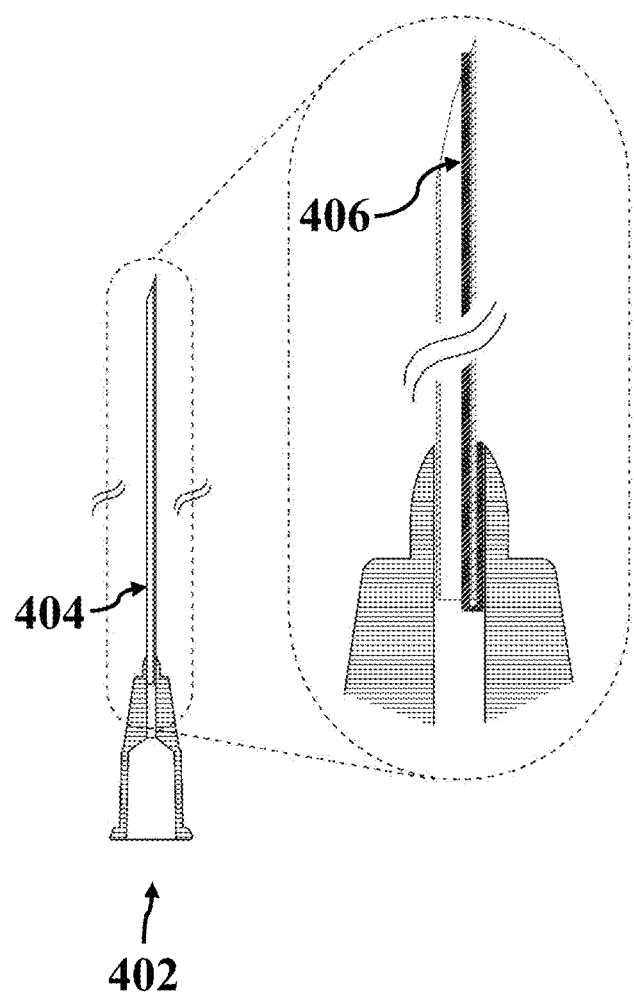
FIG. 4B illustrates a schematic side view of an exemplary instrument for diagnosis of cancer involved LNs, consistent with one or more exemplary embodiments of the present disclosure.

An exemplary instrument may be designed and fabricated to be utilized through one or more exemplary steps of methods 100, 200 and 300. FIG. 4A shows a schematic view of exemplary instrument 402 for diagnosis of cancer involved LNs, consistent with one or more exemplary embodiments of the present disclosure. In addition, for more clearance, FIG. 4B shows a schematic side view of exemplary instrument 402 for diagnosis of cancer involved LNs, consistent with one or more exemplary embodiments of the present disclosure. In an exemplary embodiment, instrument 402 may include a hypodermic needle including hollow needle 404 and an exemplary pH-sensing paper 406. In an exemplary embodiment, instrument 402 may include a hypodermic needle of an injection syringe including hollow needle 404 and exemplary pH-sensing paper 406 embedded inside hollow needle 404. In an exemplary embodiment, pH-sensing paper 406 may be placed and fixed (adhered) inside hollow needle 404.

In an exemplary embodiment, instrument 402 may be configured to allow for conducting step 306 of exemplary method 300 for putting pH-sensing paper 406 in contact with lymphatic fluid of a lymph node by inserting instrument 402 inside the lymph node. In an exemplary embodiment, instrument 402 may be configured to be attached to a syringe (i.e., an injection syringe) to allow for conducting step 308 of exemplary method 300 for injecting an exemplary buffer solution into an exemplary lymph node.

Referring back to FIG. 3, step 304 may include filling the syringe with a buffer solution. In an exemplary implementation, filling the syringe with the buffer solution may include attaching instrument 402 to the syringe and filling the syringe with a biocompatible buffer solution with a neutral pH value. In an exemplary implementation, filling the syringe with the buffer solution may include filling the syringe with a PBS buffer solution with a pH value of 7.0.

Figure 5:
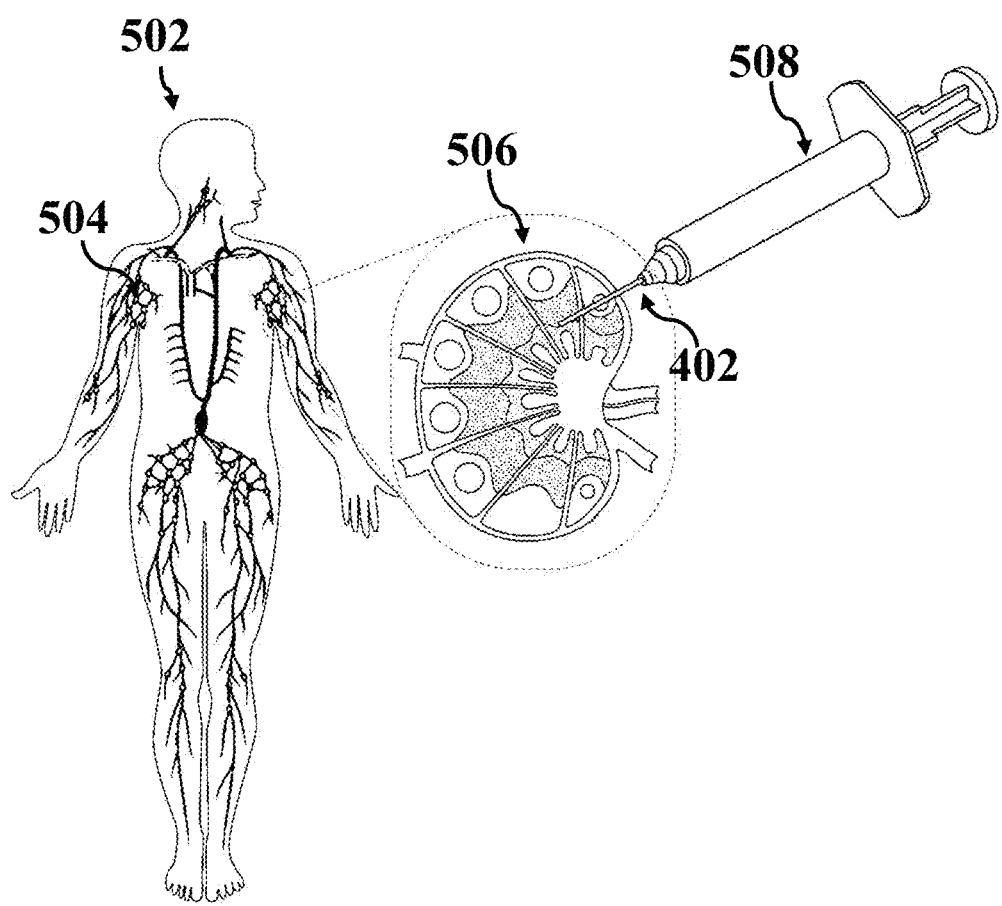
FIG. 5 illustrates a schematic view of putting an exemplary pH-sensing paper in contact with lymphatic fluid of an exemplary lymph node and/or putting the lymphatic fluid in interaction with an exemplary buffer solution, consistent with one or more exemplary embodiments of the present disclosure.

Moreover, step 306 may include putting pH-sensing paper 406 in contact with lymphatic fluid of a lymph node by inserting instrument 402 of the syringe inside the lymph node. In addition, step 308 may include putting the lymphatic fluid in interaction with the buffer solution by injecting the buffer solution into the lymph node utilizing the syringe. FIG. 5 shows a schematic view of putting pH-sensing paper 406 in contact with lymphatic fluid of exemplary lymph node 502 (step 306) and/or putting the lymphatic fluid in interaction with the buffer solution (step 306), consistent with one or more exemplary embodiments of the present disclosure. Regarding FIG. 5, instrument 402 may be attached to syringe 508 and may be utilized for conducting one or more steps of steps 304, 306, and 308.

In an exemplary implementation, syringe 508 may be filled with the buffer solution in step 304. In an exemplary implementation, step 306 may include putting pH-sensing paper 406 in contact with lymphatic fluid of exemplary lymph node 506 by inserting instrument 402 of syringe 508 into lymph node 506. In an exemplary embodiment, lymph node 506 may be a lymph node of lymphatic system 504 of person 502 who may be suspected to involve lymph cancer or have a metastatic cancer. In an exemplary implementation, step 308 may include putting the lymphatic fluid of lymph node 506 in interaction with the buffer solution by injecting the buffer solution into lymph node 506 utilizing syringe 508.

Moreover, step 310 may include detecting lymph node 506 as a cancer involved lymph node if color of pH-sensing paper 406 is changed to an acidic-range pH color. In an exemplary implementation, detecting lymph node 506 as a cancer involved lymph node (step 310) may include determining lymph node 506 as a cancer involved lymph node if color of pH-sensing paper 406 changes to the acidic-range pH color over a time period between about 5 seconds and 30 seconds. In an exemplary implementation, detecting lymph node 506 as a cancer involved lymph node (step 310) may include monitoring or recording color of pH-sensing paper 406 over a time period between about 5 seconds and 30 seconds and detecting lymph node 506 as a cancer involved lymph node if color of pH-sensing paper 406 is changed to an acidic-range pH color.

In an exemplary implementation, all steps of each of methods 100, 200, and 300 may be carried out in less than one minute; resulting in enabling real-time detection of a cancer or a metastasis. In an exemplary implementation, instrument 402 may be configured to be utilized as a metabolism based metastatic lymph diagnoser (MMLD) and may be a real-time noninvasive tool for precise and fast diagnosis of cancer involved LNs.

In an exemplary implementation, instrument 402 may be utilized through each of methods 100, 200, and 300 to detect metastatic cancer cells in lymph nodes during surgery. In an exemplary implementation, instrument 402 and each of methods 100, 200, and 300 described herein above may be utilized in a surgical process to prevent removal of healthy lymph nodes. Furthermore, instrument 402 and each of methods 100, 200, and 300 may be utilized to provide an accurate and real-time diagnosis in an operating room with no need for unnecessary secondary surgery and reducing cancer recurrences. In another exemplary implementation, instrument 402 and each of methods 100, 200, and 300 may be utilized in a radiological process to help interventional radiologist for more accurate identification of cancer involved LNs.

Example 1: Real-Time Diagnosis of Cancer Involved Lymph Nodes

In this example, an exemplary instrument (an exemplary MMLD) similar to instrument 402 was fabricated and then utilized via an exemplary method similar to method 300 for diagnosis of cancer involved LNs based on pH sensing. A micro-syringe (gauge 18, with an inner diameter of 838 μm of needle) was filled with about 100 μl of injectable sterile PBS and the syringe needle was embedded by a thin litmus paper. The mechanism included inserting the needle inside LNs, injection of PBS rubbing LNs, and checking color of litmus paper which indicated the acidity or basicity of lymph node fluid based on lipid synthesis of cancer cells in LNs. This procedure may be individually repeated utilizing three needles and if even one of the needles showed acidic pH with pH equal to or lower than 6 (as experimentally was calibrated); then, the LN was declared as a cancer involved LN. Exemplary instruments and syringes were sterilized after being manufactured under the plasma sterile protocol (Standard Number: ISO/NP 22441).

In-vitro fresh lymph node samples were prepared from 25 patients' candidate for breast cancer that were recorded from 2018-10-30 to 2019-11-30. By real-time and precise pH sensing of LNs, one might achieve a calibration pattern to distinguish normal LNs from metastatic LNs. To achieve this calibration, 100 μl PBS was injected to SLNs immediately after dissection and MMLD was entered to the SLNs. Then, pH value of lymphatic fluid was read based on the color of litmus paper and the acidity or basicity of the lymph node fluid was detected.

In addition to exemplary pH sensing based method, lymph node samples were tested and analyzed by pathologic assays via Hematoxylin and Eosin (H&E) staining which is the most routine staining procedure in histopathology. After pathological evaluation of the SLNs, the pH and cancer diagnosis result of each LN were recorded in Table 1 herein below. It should be noted that H&E staining is a combination of two dyes. Hematoxylin and Eosin are used to demonstrate the nucleus and cytoplasmic inclusions in clinical specimens. Hematoxylin, which contains Alum, stains the nucleus in light blue. In the presence of an acid, the dye turns into the red. Therefore, by treating the tissue with an acid solution, the differentiation is achieved. In the bluing step, the initial soluble is converted to red color within the nucleus to an insoluble blue color. By utilizing Eosin, the counter-staining is done, which imparts pink color to the cytoplasm. The initial step of the H&E staining process is deparaffinized a tissue section and flaming the slide on a burner and placing it in the xylene. The process treatment must be repeated afterward, and the hydration process should be done. To hydrate a tissue section, one should pass it through a decreasing concentration of alcohol baths and water (100%, 90%, 80%, and 70%). Then, the sample should be stained in hematoxylin for approximately 3 to 5 minutes, in the next step, it should be washed in running tap water until sections "blue" for 5 minutes or less. In the next level, the sample should be placed in 1% acid alcohol (1% HCL in 70% alcohol) for 5 minutes. Subsequently, the sample should be washed in running tap water until it turns into blue again by dipping in an alkaline solution (e.g., ammonia water) followed by tap water washing process. Furthermore, in 1% Eosin Y for 10 minutes, the sample is stained and should be washed in tap water for 1-5 minutes. Finally, to dehydrate the sample, one should dip it in increasing concentration of alcohol and clear in xylene.

Exemplary pH sensing based method was tested on 65 lymph nodes immediately after dissection (through standard guidelines) from 25 breast cancer patients. Some of them were normal and some others were metastatic due to pathological evaluations (Table 1). Changes in pH value of LNs from more than 7 in healthy LNs to less than 6 in cancerous ones, may indicate well differentiation ability of lymphatic fluid (LF) pH as metastasis indicator. Results obtained by exemplary MMLD were compared by frozen section diagnostics based on permanent H&E of lymph nodes as a gold standard. Regarding Table 1, positive samples are indicated with positive sign (+) and negative samples are indicated with negative sign (−). Among 65 samples, MMLD had only 1 false-positive and 1 false-negative for patient's ID 16 (sample ID 48) and patient's ID 5 (sample ID 12). This test was individually repeated by three needles and if even one of the needles showed acidic pH with pH lower than 6.0 (as experimentally was calibrated), then exemplary tested LN was declared as a cancer involved LN.

TABLE 1

Direct comparisons between MMLD responses and pathological assay, representing pH values measured by MMLD for lymph node samples versus pathological diagnoses of 25 breast cancer patients.

| Patient ID # | Patient samples # | Type of lymph node | MMLD diagnosis (pH value) | Frozen pathology diagnosis | Permanent pathology diagnosis | Sensor response compare to Permanent pathology (gold standard) |
|---|---|---|---|---|---|---|
| 1 | 1 | Sentinel | 4.0 | + | + | TP |
| 1 | 2 | Auxiliary 1 | 5.0 | + | + | TP |
| 1 | 3 | Auxiliary 2 | 7.0 | − | − | TN |
| 1 | 4 | Auxiliary 3 | 10.0 | − | − | TN |
| 1 | 5 | Auxiliary 4 | 7.0 | − | − | TN |
| 1 | 6 | Auxiliary 5 | 8.0 | − | − | TN |
| 1 | 7 | Auxiliary 6 | 8.0 | − | − | TN |
| 2 | 8 | Sentinel 1 | 8.0 | − | − | TN |
| 2 | 9 | Sentinel 2 | 7.0 | − | − | TN |
| 3 | 10 | Sentinel | 7.0 | − | − | TN |
| 4 | 11 | Sentinel | 10.0 | − | − | TN |
| 5 | 12 | Sentinel | 7.0 | − | + | FN |
| 5 | 13 | Auxiliary 1 | 7.0 | − | − | TN |
| 5 | 14 | Auxiliary 2 | 7.0 | − | − | TN |
| 5 | 15 | Auxiliary 3 | 7.0 | − | − | TN |
| 5 | 16 | Auxiliary 4 | 9.0 | − | − | TN |
| 5 | 17 | Auxiliary 5 | 8.0 | − | − | TN |
| 5 | 18 | Auxiliary 6 | 8.0 | − | − | TN |
| 6 | 19 | Sentinel | 10.0 | − | − | TN |
| 7 | 20 | Sentinel | 10.0 | − | − | TN |
| 8 | 21 | Sentinel | 7.0 | − | − | TN |
| 9 | 22 | Sentinel | 7.0 | − | − | TN |
| 10 | 23 | Sentinel | 4.0 | + | + | TP |
| 10 | 24 | Auxiliary 1 | 5.5 | + | + | TP |
| 10 | 25 | Auxiliary 2 | 6.0 | − | + | TP |
| 10 | 26 | Auxiliary 3 | 7.0 | − | − | TN |
| 10 | 27 | Auxiliary 4 | 7.0 | − | − | TN |
| 10 | 28 | Auxiliary 5 | 8.0 | − | − | TN |
| 10 | 29 | Auxiliary 6 | 8.0 | − | − | TN |
| 11 | 30 | Sentinel | 7.0 | − | − | TN |
| 12 | 31 | Sentinel 1 | 4.0 | + | + | TP |
| 12 | 32 | Sentinel 2 | 5.0 | + | + | TP |
| 12 | 33 | Auxiliary 1 | 6.0 | + | + | TP |
| 12 | 34 | Auxiliary 2 | 6.0 | + | + | TP |
| 12 | 35 | Auxiliary 3 | 10.0 | − | − | TN |
| 12 | 36 | Auxiliary 4 | 8.0 | − | − | TN |
| 12 | 37 | Auxiliary 5 | 8.0 | − | − | TN |
| 12 | 38 | Auxiliary 6 | 10.0 | − | − | TN |
| 13 | 39 | Sentinel | 10.0 | − | − | TN |
| 14 | 40 | Sentinel | 7.0 | − | − | TN |
| 15 | 41 | Sentinel | 6.0 | + | + | TP |
| 15 | 42 | Auxiliary 1 | 8.0 | − | − | TN |
| 15 | 43 | Auxiliary 2 | 9.0 | − | − | TN |
| 15 | 44 | Auxiliary 3 | 9.0 | − | − | TN |
| 15 | 45 | Auxiliary 4 | 7.0 | − | − | TN |
| 15 | 46 | Auxiliary 5 | 7.0 | − | − | TN |
| 15 | 47 | Auxiliary 6 | 7.0 | − | − | TN |
| 16 | 48 | Sentinel | 6.0 | − | − | FP |
| 17 | 49 | Sentinel | 8.0 | − | − | TN |
| 18 | 50 | Sentinel | 8.0 | − | − | TN |
| 19 | 51 | Sentinel | 5.0 | + | + | TP |
| 19 | 52 | Auxiliary 1 | 7.0 | − | − | TN |
| 19 | 53 | Auxiliary 2 | 7.0 | − | − | TN |
| 19 | 54 | Auxiliary 3 | 10.0 | − | − | TN |
| 19 | 55 | Auxiliary 4 | 10.0 | − | − | TN |
| 19 | 56 | Auxiliary 5 | 7.0 | − | − | TN |
| 19 | 57 | Auxiliary 6 | 8.0 | − | − | TN |

TABLE 1-continued

Direct comparisons between MMLD responses and pathological assay, representing pH values measured by MMLD for lymph node samples versus pathological diagnoses of 25 breast cancer patients.

| Patient ID # | Patient samples # | Type of lymph node | MMLD diagnosis (pH value) | Frozen pathology diagnosis | Permanent pathology diagnosis | Sensor response compare to Permanent pathology (gold standard) |
|---|---|---|---|---|---|---|
| 20 | 58 | Sentinel 1 | 7.0 | – | – | TN |
| 20 | 59 | Sentinel 2 | 7.0 | – | – | TN |
| 21 | 60 | Sentinel | 9.0 | – | – | TN |
| 22 | 61 | Sentinel | 8.0 | – | – | TN |
| 23 | 62 | Sentinel | 7.0 | – | – | TN |
| 24 | 63 | Sentinel 1 | 7.0 | – | – | TN |
| 24 | 64 | Sentinel 2 | 10.0 | – | – | TN |
| 25 | 65 | Sentinel | 8.0 | – | – | TN |

MMLD showed about 90% selectivity and 92% sensitivity for detecting cancer cells metastasized to lymph nodes while this value in conventional frozen pathology was both about 83% as presented in Table 2 herein below.

TABLE 2

Comparative diagnostic results of the MMLD and Frozen pathology based on the permanent pathology as a gold standard for 65 LNs samples from 25 patients

| Diagnosis Results of the LNs (65 samples from 25 breast cancer patients) | MMLD | Frozen |
|---|---|---|
| TP | 11 | 10 |
| TN | 52 | 53 |
| FP | 1 | 0 |
| FN | 1 | 2 |
| Sensitivity | 92% | 83% |
| Specificity | 98% | 1 |
| Selectivity | 90% | 83% |

(TP: True Positive,
FP: False Positive,
TN: True Negative, and
FN: False Negative).

Figure 6:
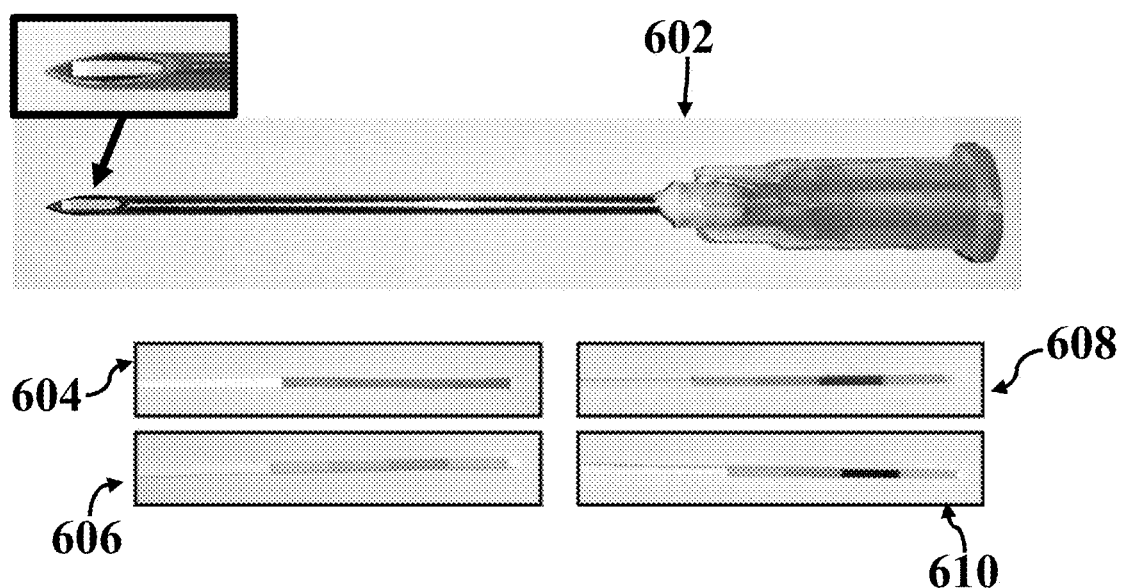
FIG. 6 shows an exemplary metabolism based metastatic lymph diagnoser (MMLD) instrument and exemplary detected responses to pH sensing of sentinel lymph node (SLN) secreted fluid recorded on pH sensing papers, consistent with one or more exemplary embodiments of the present disclosure.

FIG. 6 shows an exemplary MMLD instrument 602 fabricated similar to exemplary instrument 402 and exemplary detected responses to pH sensing of secreted fluid from SLNs recorded on pH sensing papers 604, 606, 608, and 610, consistent with one or more exemplary embodiments of the present disclosure. Exemplary MMLD instrument 602 was utilized according to method 300 for detection of acidic or basic in lymph node secretion solution. Exemplary MMLD responses to pH sensing of the lymph secreted solution shows that color of pH-indicator strips changes from a neutral color to an acidic range (less than pH value of about 6) for cancer involved SLNs as shown in images 604 and 606. Whereas, color of pH-indicator strips remains neutral or changes from a neutral color to a basic range (a pH value between about 7 and about 10) for healthy SLNs (images 608 and 610). The measured pH of the SLN fluid secreted in cancerous lymph nodes was less than 6 and for healthy ones were 7-10, respectively.

Figure 7:
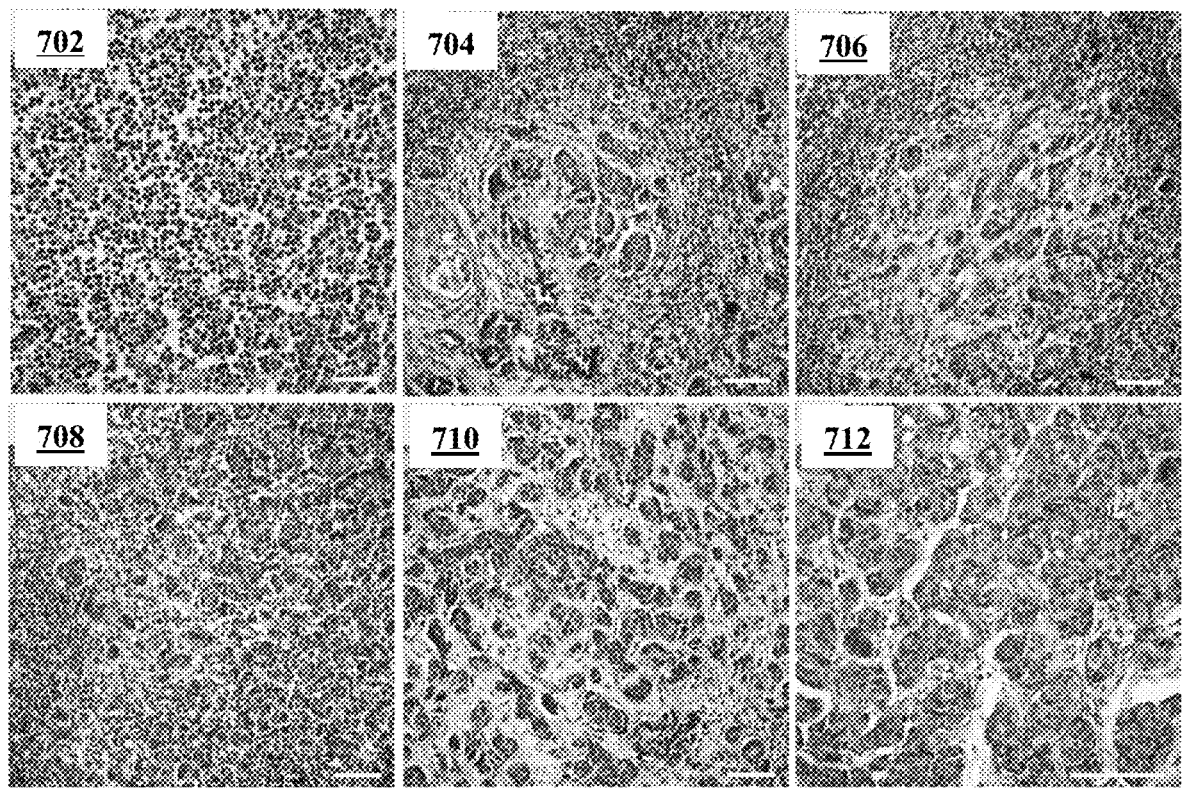
FIG. 7 shows Hematoxylin and Eosin (H&E) images of normal and cancerous lymph nodes with different percentage of involved cancer cells, consistent with one or more exemplary embodiments of the present disclosure.

Furthermore, FIG. 7 shows H&E images of normal and cancerous lymph nodes with different percentage of involved cancer cells, consistent with one or more exemplary embodiments of the present disclosure. Image 702 shows H&E image of a normal (healthy) lymph node (pH=10; patient ID 4 and sample ID 11). Image 704 shows H&E image of lymph node with about 20% cancer cells (pH=6; patient ID 15 and sample ID 41). Image 706 shows H&E image of lymph node with about 50% cancer cells (pH=5.5; patient ID 10 and sample ID 24). Image 708 shows H&E image of lymph node with about 85% of cancer cells (pH=5; patient ID 12 and sample ID 32). Image 710 shows H&E image of lymph node with about 90% (pH=4; patient ID 12 and sample ID 31), and Image 712 shows H&E image of lymph node with more than about 95% of cancer cells (pH=4; patient ID 1 and sample ID 1). It should be noted that in these images each bar is equal to 100 µm.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for detecting cancer involved lymph nodes, comprising:
   in vivo measuring pH value of lymphatic fluid of a lymph node, comprising:
      placing a pH-sensing paper inside a hollow needle of an injection syringe by adhering the pH-sensing paper inside the hollow needle, one end of the pH-sensing paper at a tip of the hollow needle being in contact with a surrounding environment of the hollow needle;
      filling the injection syringe with a buffer solution;
      putting the pH-sensing paper in in-situ contact with lymphatic fluid of the lymph node inside the lymph node by putting the one end of the pH-sensing paper inside the lymph node via inserting the tip of the hollow needle of the injection syringe inside the lymph node; and
      putting the lymphatic fluid in interaction with the buffer solution by injecting the buffer solution through the hollow needle of the injection syringe into the lymph node utilizing the injection syringe, the interacted lymphatic fluid of the lymph node with the buffer solution being in contact with the one end of the pH-sensing paper; and
   detecting the lymph node being a cancer involved lymph node responsive to the measured pH value of the lymphatic fluid of the lymph node being less than 7.0 by detecting changing color of the pH-sensing paper to an acidic-range pH color.

2. The method of claim 1, wherein injecting the buffer solution into the lymph node comprises injecting a sterile buffer solution of phosphate-buffered saline (PBS) into the lymph node.

3. The method of claim 2, wherein injecting the sterile buffer solution into the lymph node comprises injecting at least 100 μL of the sterile buffer solution of PBS into the lymph node.

4. The method of claim 1, wherein injecting the buffer solution into the lymph node comprises injecting the buffer solution into a lymph node located at least one of armpits, digestive system, groin, neck, and combinations thereof.

5. The method of claim 1, wherein injecting the buffer solution into the lymph node comprises at least one of in vitro injecting the buffer solution into the lymph node and in vivo injecting the buffer solution into the lymph node.

6. The method of claim 1, wherein detecting the lymph node being a cancer involved lymph node comprises:
   detecting changes in color of the pH-sensing paper for a time period between 5 seconds and 30 seconds after injecting the buffer solution into the lymph node; and
   detecting the lymph node being a cancer involved lymph node responsive to detecting a change in color of the pH-sensing paper to an acidic-range pH color.

7. The method of claim 1, wherein the needle of the injection syringe comprises a hypodermic needle with a gauge size 18.

8. The method of claim 1, wherein injecting the buffer solution into the lymph node comprises injecting a biocompatible sterile buffer solution with a neutral pH value into the lymph node.

9. The method of claim 1, wherein detecting the lymph node being a cancer involved lymph node comprises detecting the lymph node being a cancer involved lymph node responsive to the measured pH value of the lymphatic fluid of the lymph node being less than 6.0.

* * * * *